US009023987B2

(12) United States Patent
Chung et al.

(10) Patent No.: US 9,023,987 B2
(45) Date of Patent: May 5, 2015

(54) CELL-PERMEABLE PEPTIDE

(75) Inventors: Chong-Pyoung Chung, Seoul (KR); Yoon-Jeong Park, Seoul (KR); Jue-Yeon Lee, Gyeonggi-do (KR); Jin Sook Suh, Seoul (KR)

(73) Assignees: Seoul National University R&DB Foundation, Seoul (KR); Nano Intelligent Biomedical Engineering Corporation Co., Ltd., Seoul (KR)

( * ) Notice: Subject to any disclaimer, the term of this patent is extended or adjusted under 35 U.S.C. 154(b) by 49 days.

(21) Appl. No.: 13/821,790

(22) PCT Filed: Apr. 25, 2011

(86) PCT No.: PCT/KR2011/002990
§ 371 (c)(1),
(2), (4) Date: May 16, 2013

(87) PCT Pub. No.: WO2012/033272
PCT Pub. Date: Mar. 15, 2012

(65) Prior Publication Data
US 2013/0237484 A1    Sep. 12, 2013

(30) Foreign Application Priority Data
Sep. 9, 2010    (KR) .................. 10-2010-0088610

(51) Int. Cl.
*C07K 9/00* (2006.01)
*C07K 14/435* (2006.01)
*C07K 14/51* (2006.01)
*C07K 7/06* (2006.01)
*C07K 7/08* (2006.01)
*A61K 38/00* (2006.01)

(52) U.S. Cl.
CPC .............. *C07K 14/435* (2013.01); *C07K 14/51* (2013.01); *C07K 7/06* (2013.01); *C07K 7/08* (2013.01); *A61K 38/00* (2013.01)

(58) Field of Classification Search
CPC ........................................................ C07K 9/00
USPC ......................................................... 530/327
See application file for complete search history.

(56) References Cited

U.S. PATENT DOCUMENTS

| 7,504,374 | B2 | 3/2009 | Marx et al. | |
| 2009/0234100 | A9 * | 9/2009 | Boden et al. | 530/350 |

OTHER PUBLICATIONS

Futaki et al. Arginine-rich peptides—an abundant source of membrane-permeable peptides having potential as carriers for intracellular protein delivery. Journal of Biological Chemistry. 2001, 276(8): 5836-5840.*

Wu et al. Hexahistidine (His6)-tag dependent protein dimerization: a cautionary tale. Acta Biochimica Polonica. 1999; 46(3): 591-599.*
Boden, S., et al., "LMP-1, A LIM-Domain Protein, Mediates BMP-6 Effects on Bone Formation", "Endocrinology", 1998, pp. 5125-5134, vol. 139, No. 12.
Celeste, A., et al., "Identification of transforming growth factor beta family members present in bone-inductive protein purified from bovine bone", "Proc. Natl. Acad. Sci. USA", Dec. 1990, pp. 9843-9847, vol. 87.
Fawell, S., et al., "Tat-mediated delivery of heterologous proteins into cells", "Proc. Natl. Acad. Sci. USA", Jan. 1994, pp. 664-668, vol. 91.
Herce, H., et al., "Arginine-Rich Peptides Destabilize the Plasma Membrane, Consistent with a Pore Formation Translocation Mechanism of Cell-Penetrating Peptides", "Biophysical Journal", Oct. 2009, pp. 1917-1925, vol. 97.
Kim, C., et al., "The Effect of Recombinant Human Bone Morphogenetic Protein-4 on the Osteoblastic Differentiation of Mouse Calvarial Cells Affected by Porphyromonas gingivalis", "J. Periodontol.", Oct. 2002, pp. 1126-1132, vol. 73, No. 10.
Kingsley, D., et al., "The Mouse short ear Skeletal Morphogenesis Locus Is Associated with Defects in a Bone Morphogenetic Member of the TGFbeta Superfamily", "Cell", Oct. 30, 1992, pp. 399-410, vol. 71.
Laus, R., et al., "Enhanced major histocompatibility complex class I-dependent presentation of antigens modified with cationic and fusogenic peptides", "Nature Biotechnology", Dec. 2000, pp. 1269-1272, vol. 18.
Sangadala, S., et al., "LIM Mineralization Protein-1 Potentiates Bone Morphogenetic Protein Responsiveness via a Novel Interaction with Smurf1 Resulting in Decreased Ubiquitination of Smads", "The Journal of Biological Chemistry", Jun. 23, 2006, pp. 17212-17219, vol. 281, No. 25.
Schwarze, S., et al., "In vivo protein transduction: intracellular delivery of biologically active proteins, compounds and DNA", "Trends in Pharmacological Sciences", Feb. 2000, pp. 45-48, vol. 21.
Sebbage, V., "Cell-penetrating peptides and their therapeutic applications", "Bioscience Horizons", Mar. 2009, pp. 64-72, vol. 2, No. 1.

(Continued)

Primary Examiner — Prema Mertz
(74) Attorney, Agent, or Firm — Hultquist, PLLC; Steven J. Hultquist; Mary B. Grant

(57) ABSTRACT

The present invention relates to a novel human-derived cell permeable peptide-bioactive peptide conjugate and the use thereof. According to the present invention, cationic cell permeable peptides derived from human bone morphogenetic protein-4 have no toxicity and immunogenicity and thus exhibit high stability as compared to viral peptide delivery vehicles, and can transport cell impermeable material into cells and into an organism without any damage to cell or material, thereby significantly increasing target gene expression. In addition, the peptide may be applied to clinical use without having to undergo a large number of processes and mass-produced, such that the present invention may be useful in the development of a drug delivery system and treatment technologies using said peptide.

1 Claim, 6 Drawing Sheets

(56) References Cited

OTHER PUBLICATIONS

Shin, J., et al., "PIF3 regulates anthocyanin biosynthesis in an HY5-dependent manner with both factors directly binding anthocyanin biosynthetic gene promoters in Arabidopsis", "The Plant Journal", Feb. 22, 2007, pp. 981-994, vol. 49.

Wikesjoe, U., et al., "Periodontal repair in dogs: effect of rhBMP-2 concentration on regeneration of alveolar bone and periodontal attachment", "J Clin Periodontol", 1999, pp. 392-400, vol. 26.

Wozney, J., et al., "Novel Regulators of Bone Formation: Molecular Clones and Activities", "Science", Dec. 16, 1988, pp. 1528-1534, vol. 242.

* cited by examiner

SEQUENCE LISTING

```
<160> NUMBER OF SEQ ID NOS: 25

<210> SEQ ID NO 1
<211> LENGTH: 12
<212> TYPE: PRT
<213> ORGANISM: Artificial
<220> FEATURE:
<223> OTHER INFORMATION: H4S

<400> SEQUENCE: 1

Ser Ser Arg Lys Lys Asn Pro Asn Cys Arg Arg His
1               5                   10

<210> SEQ ID NO 2
<211> LENGTH: 13
<212> TYPE: PRT
<213> ORGANISM: Artificial
<220> FEATURE:
<223> OTHER INFORMATION: H4Q

<400> SEQUENCE: 2

Gln Arg Ala Arg Lys Lys Asn Lys Asn Cys Arg Arg His
1               5                   10

<210> SEQ ID NO 3
<211> LENGTH: 13
<212> TYPE: PRT
<213> ORGANISM: Artificial
<220> FEATURE:
<223> OTHER INFORMATION: HBD-3P

<400> SEQUENCE: 3

Cys Ser Thr Arg Gly Arg Lys Cys Cys Arg Arg Lys Lys
1               5                   10

<210> SEQ ID NO 4
<211> LENGTH: 15
<212> TYPE: PRT
<213> ORGANISM: Artificial
<220> FEATURE:
<223> OTHER INFORMATION: H2

<400> SEQUENCE: 4
```

```
His Lys Arg Glu Lys Arg Gln Ala Lys His Lys Gln Arg Lys Arg
1               5                   10                  15

<210> SEQ ID NO 5
<211> LENGTH: 15
<212> TYPE: PRT
<213> ORGANISM: Artificial
<220> FEATURE:
<223> OTHER INFORMATION: H3

<400> SEQUENCE: 5

Lys Ser Lys Asn Lys Lys Gln Arg Lys Gly Pro His Arg Lys
1               5                   10                  15

<210> SEQ ID NO 6
<211> LENGTH: 12
<212> TYPE: PRT
<213> ORGANISM: Artificial
<220> FEATURE:
<223> OTHER INFORMATION: H3B

<400> SEQUENCE: 6

Lys Pro Arg Pro Gly Arg Lys Asp Arg Lys Lys
1               5                   10

<210> SEQ ID NO 7
<211> LENGTH: 13
<212> TYPE: PRT
<213> ORGANISM: Artificial
<220> FEATURE:
<223> OTHER INFORMATION: H4-1

<400> SEQUENCE: 7

Arg Arg Arg Arg Ala Lys Arg Ser Pro Lys His His Ser
1               5                   10

<210> SEQ ID NO 8
<211> LENGTH: 10
<212> TYPE: PRT
<213> ORGANISM: Artificial
<220> FEATURE:
<223> OTHER INFORMATION: H6

<400> SEQUENCE: 8

Ser Arg Arg Arg Gln Gln Ser Arg Asn Arg
1               5                   10

<210> SEQ ID NO 9
<211> LENGTH: 14
<212> TYPE: PRT
<213> ORGANISM: Artificial
<220> FEATURE:
<223> OTHER INFORMATION: HB

<400> SEQUENCE: 9

Arg Ala Val Arg Pro Leu Arg Arg Arg Gln Pro Lys Lys Ser
1               5                   10

<210> SEQ ID NO 10
<211> LENGTH: 13
<212> TYPE: PRT
<213> ORGANISM: Artificial
<220> FEATURE:
<223> OTHER INFORMATION: H4C

<400> SEQUENCE: 10

Cys Ser Ser Arg Lys Lys Asn Pro Asn Cys Arg Arg His
```

```
<210> SEQ ID NO 11
<211> LENGTH: 14
<212> TYPE: PRT
<213> ORGANISM: Artificial
<220> FEATURE:
<223> OTHER INFORMATION: H5C

<400> SEQUENCE: 11

Cys Ser Ser Arg Lys Lys Asn Lys Asn Cys Pro Arg Arg His
1               5                   10

<210> SEQ ID NO 12
<211> LENGTH: 14
<212> TYPE: PRT
<213> ORGANISM: Artificial
<220> FEATURE:
<223> OTHER INFORMATION: H6C

<400> SEQUENCE: 12

Cys Ser Ser Arg Lys Lys Asn Pro Asn Cys Pro Arg Arg His
1               5                   10

<210> SEQ ID NO 13
<211> LENGTH: 10
<212> TYPE: PRT
<213> ORGANISM: Artificial
<220> FEATURE:
<223> OTHER INFORMATION: osteoinductive sequence

<400> SEQUENCE: 13

Gly Ala Pro Pro Pro Ala Asp Ser Ala Pro
1               5                   10

<210> SEQ ID NO 14
<211> LENGTH: 4
<212> TYPE: PRT
<213> ORGANISM: Artificial
<220> FEATURE:
<223> OTHER INFORMATION: osteoinductive sequence

<400> SEQUENCE: 14

Pro Pro Gly Tyr
1

<210> SEQ ID NO 15
<211> LENGTH: 4
<212> TYPE: PRT
<213> ORGANISM: Artificial
<220> FEATURE:
<223> OTHER INFORMATION: osteoinductive sequence

<400> SEQUENCE: 15

Pro Pro Ala Tyr
1

<210> SEQ ID NO 16
<211> LENGTH: 11
<212> TYPE: PRT
<213> ORGANISM: Artificial
<220> FEATURE:
<223> OTHER INFORMATION: anticare peptide sequence

<400> SEQUENCE: 16

Thr Arg Gly Arg Lys Cys Cys Arg Arg Lys Lys
1               5                   10
```

```
<210> SEQ ID NO 17
<211> LENGTH: 22
<212> TYPE: PRT
<213> ORGANISM: Artificial
<220> FEATURE:
<223> OTHER INFORMATION: H4S-osteoinductive sequence

<400> SEQUENCE: 17

Gly Ala Pro Pro Ala Asp Ser Ala Pro Ser Ser Arg Lys Lys Asn
1               5                   10                  15

Pro Asn Cys Arg Arg His
            20

<210> SEQ ID NO 18
<211> LENGTH: 19
<212> TYPE: DNA
<213> ORGANISM: Artificial
<220> FEATURE:
<223> OTHER INFORMATION: alkaline phosphatase (ALP)_FP

<400> SEQUENCE: 18
gacccttgac ccccacaat                                                    19

<210> SEQ ID NO 19
<211> LENGTH: 21
<212> TYPE: DNA
<213> ORGANISM: Artificial
<220> FEATURE:
<223> OTHER INFORMATION: alkaline phosphatase (ALP)_RP

<400> SEQUENCE: 19
gctcgtactg catgtccccc t                                                 21

<210> SEQ ID NO 20
<211> LENGTH: 16
<212> TYPE: DNA
<213> ORGANISM: Artificial
<220> FEATURE:
<223> OTHER INFORMATION: Osteocalcin (OCN)_FP

<400> SEQUENCE: 20
gaagcccagc ggtgca                                                       16

<210> SEQ ID NO 21
<211> LENGTH: 18
<212> TYPE: DNA
<213> ORGANISM: Artificial
<220> FEATURE:
<223> OTHER INFORMATION: Osteocalcin (OCN)_RP

<400> SEQUENCE: 21
cactacctcg ctgcctcc                                                     18

<210> SEQ ID NO 22
<211> LENGTH: 21
<212> TYPE: DNA
<213> ORGANISM: Artificial
<220> FEATURE:
<223> OTHER INFORMATION: Runt-related transcription factor 2 (RUNX2)_FP

<400> SEQUENCE: 22
ccggcaagat gagcgaggtc a                                                 21

<210> SEQ ID NO 23
```

```
<211> LENGTH: 21
<212> TYPE: DNA
<213> ORGANISM: Artificial
<220> FEATURE:
<223> OTHER INFORMATION: Runt-related transcription factor 2 (RUNX2)_RP

<400> SEQUENCE: 23
gtgggttgga gaagcggctc t                                              21

<210> SEQ ID NO 24
<211> LENGTH: 18
<212> TYPE: DNA
<213> ORGANISM: Artificial
<220> FEATURE:
<223> OTHER INFORMATION: Glyceraldehyde-3-phosphate dehydrogenase
      (GAPDH)_FP

<400> SEQUENCE: 24
gaaggtgaag gtcggagt                                                  18

<210> SEQ ID NO 25
<211> LENGTH: 20
<212> TYPE: DNA
<213> ORGANISM: Artificial
<220> FEATURE:
<223> OTHER INFORMATION: Glyceraldehyde-3-phosphate dehydrogenase
      (GAPDH)_RP

<400> SEQUENCE: 25
gaagatggtg atgggatttc                                                20
```

CELL-PERMEABLE PEPTIDE

CROSS-REFERENCE TO RELATED APPLICATIONS

This application is a U.S. national phase under the provisions of 35 U.S.C. §371 of International Patent Application No. PCT/KR2011/002990 filed Apr. 25, 2011, which in turn claims priority of Korean Patent Application No. 10-2010-0088610 filed Sep. 9, 2010. The disclosures of such international patent application and Korean priority patent application are hereby incorporated herein by reference in their respective entireties, for all purposes.

TECHNICAL FIELD

The present invention relates to a novel human-derived cell permeable peptide-bioactive peptide conjugate and the use thereof, and more particularly, to cell permeable peptide-bioactive peptide conjugate capable of directly permeate into a target cell to function as therapeutic peptides by chemically binding cell permeable peptide to a bioactivity inducing sequences selected from a group consisting of a bone differentiation inducing sequence, a bone regeneration inducting sequence, and an anti-inflammation functional sequence to thereby directly introduce an important domain of an impermeable intracellular protein having a bioactivity into cells, and to a pharmaceutical composition for treatment containing the same. The present inventors named this study as Target Oriented Peptide Therapeutics Discovery (TOPscovery).

BACKGROUND ART

Slight bone damage, such as a fracture, or the like, may be cured by simple surgical treatment, but there are bone diseases such as nonunion, delayed union, bone loss, bone necrosis, or the like, for which it is difficult to find alternatives except for autogenous bone graft since access to osteoblast cells is fundamentally difficult, or the number of cells or activity thereof are insufficient. A treatment method using osteoblast cells cultured in vitro is recognized as a new alternatives to solve this difficulty. The osteoblast cells are derived from mesenchymal stem cells and may be partially obtained from normal bone, fat, blood, or the like, but a harvest site at which minimally invasive harvest and the maximum yield of cells may be expected is bone marrow. In the bone marrow, a large amount of bone marrow stromal cells referred to as the mesenchymal stem cells are present as well as blood-related cells. A technology of regenerating bone using the bone marrow stromal cells may be largely classified into 1) a technology of using bone marrow itself, 2) a technology of separating only nucleated cells from the bone marrow to use them, 3) a technology of proliferating the bone marrow stromal cells to use them as a cell therapy product, 4) a technology of proliferating and differentiating the bone marrow stromal cells into osteoblast cells to use them as a cell therapy product, and the like. Some of them were developed, and some of them have been currently developed.

In order to induce bone regeneration using the cells as described above, a growth factor capable of stimulating and promoting signal transduction pathways for bone differentiation has been demanded. In addition, in osteoarthritis, rheumatoid arthritis, a bioactive material capable of curing damaged cartilage and regenerating bone tissues at the same time in addition to controlling inflammation has been demanded. Through many studies, it was known that human recombinant bone morphogenetic proteins (rhBMPs) forms new bone and new cartilage as a TGF-β super-family when rhBMPs is grafted ((Wozney J M et al., Science 1988; 242:1528-1534; Celeste A J et al., Proc. Natl. Acad. Sci. US 1990; 87:9843-9847). Currently, 20 or more BMPs were discovered, and among them, rhBMP-2, -4, -5, -6, -7 (Kim C S et al., J Periodontal 2002; 73:1126-1132; Wikesjo U M et al., J Clin Periodontal 1999; 26:392-400; Kingsley D M et al., Cell 1992; 71:399-410), and the like, have excellent osteoinductive ability to thereby be used in a bone tissue engineering field. Nevertheless, at the time of applying the BMP to patients wanting the bone regeneration therapy, the BMP should be used at a significantly high concentration ((1.5 mg/ml) and a cost thereof is expensive, such that it is difficult to clinically apply the BMP. However, an innovative protein capable of replacing the BMP was found in 1998, and it was reported that the protein, which is referred to as intercellular LIM Mineralization Protein (LMP)1 acting in cells, is directly involved with differentiation of osteoblast (Boden S D et al., Endocrinology 1998; 139:5125-34). This protein has sites capable of binding with two WW domains in an osteoinductive region, wherein the portion binds to the WW domain of Smad ubiquitin regulatory factor (Smurf)1 decomposing Smad1 and Smad5 that are the main proteins for signal transduction pathways involved in bone differentiation. In the study reported in 2006, it was confirmed that when affinity of the LMP1 to Smurf1 are compared with those of Smad1, and Smad5, the affinity of Smurf1-LMP1 are higher than those of Smurf1-Smad1 or Smurf1-Smad5, and the shortest sequence capable of inducing differentiation into the osteoblast cell and bone formation in a WW domain binging site of LMP1 was identified (GAPPPADSAP, Boden S D et al., JBC 2006; 281: 17212-17219).

However, in order to synthesize the domain having strong hydrophobicity in vitro to induce the bone regeneration, the domain has an activity only when the domain is permeated into cells in which smurf1 is present. As a result of the studies for solving this problem, a protein transduction domain (PTD) was suggested. Recently, studies of the protein transduction domain (PTD) capable of effectively transporting a protein which it is difficult to permeate through a cell membrane into the cell have been actively conducted. It is known that this protein transduction domain (PTD), which is a short peptide with positive charge, may permeate through cell membranes and effectively transport DNA, RNA, fat, carbohydrates, compounds, or virus into cells, in addition to protein. The principle that the PTD permeates through the cell membrane is not found yet, but is thought to be independent on a receptor, endocytosis, or phagocytosis. This cell membrane permeation phenomenon of the peptide shows that movement of therapeutic proteins, which is difficult to be used as a drug due to a short half-life in vivo, and movement of genes, which are macromolecules, may be improved, such that pharmaceutical effects thereof may be improved.

Among them, studies of TAT protein, which is a human immunodeficiency virus-1 (HIV-1) transcription factor have been mainly conducted. It was found that the TAT protein is more effective in passing through the cell membrane, when the protein consists of some of 47th to 57th amino acid sequence (YGRKKRRQRRR) on which positive charged amino acid are intensively distributed, as compared to when the protein has a complete form consisting of 86 amino acids (Fawell, S et al., Proc. Natl. Acad. Sci. USA, 91:664, 1994). It was reported that TAT PTD may permeate alone or be attached to another protein to permeate through the cell membrane, and transport protein of 10 to 120 KDa regardless of the receptors into cell (Schwarze S R. et al., Trends Pharmacol Sci 2000; 21:45-48; Fawell S et al., Proc. Natl. Acad. Sci. USA 1994; 91:664-668).

As another example of peptides of which effects as cell penetrating peptide (CPP) are confirmed, there are peptides having an amino acid sequence from 267th to 300th amino acid of herpes simplex virus type 1 (HSV-1) VP22 protein (Elliott, G. et al., Cell, 88:223, 1997), peptides having an amino acid sequence from 84th to 92th amino acid of HSV-2 UL-56 protein (GeneBank code:D1047[gi:221784]), peptides having an amino acid sequence of 339th to 355th amino acid of antennapedia (ANTP) protein of *Drosophila* sp. (Schwarze, S. R. et al., Trends. Pharmacol. Sci., 21:45, 2000), and the like. In addition, effects of artificial peptides consisting of positively charged amino acids were also confirmed (Laus, R. et al., Nature Biotechnol., 18:1269, 2000).

Since it was found that in the case in which the CPP according to the related art is connected to another peptide or protein, the CPP effectively transport the fused protein into cells, various applications using the CPP were tried (Korean Patent Registration No. 10-0568457). However, since the cell permeable peptide is derived from a virus, there is a problem in view of safety.

Therefore, the technology development for safe peptides capable of regenerating bone and treating diseases including inflammatory diseases through optimal target orientation, instead of the existing virus derived peptide receptor has been urgently demanded, but research achievements are still insufficient.

Therefore, the present inventors have studied in order to synthesize a safe cell permeable peptide capable of treating diseases including bone diseases, inflammatory diseases, and excellent target specificity. As a result, the present inventors newly synthesized human bone morphogenic protein-4 derived heparin binding domain (HBD; SSRKKNPNCRRH) containing a large amount of cationic amino acids such as arginine, and the like, as a cell permeable domain, identified that impermeable domains may be effectively transported into cells using this cell permeable peptide, and confirmed that intracellular transport of a target active domain and expression of a target gene may be significantly increased by using this peptide as the peptide for transporting the active domain into the cell, thereby completing the present invention.

DISCLOSURE OF INVENTION

An object of the present invention is to provide a human-derived cell permeable peptide, which is a new cell permeable peptide capable of transporting a cell impermeable material into cell or in body.

Another object of the present invention is to provide uses of the cell permeable peptide for transporting the cell-impermeable material.

Another object of the present invention is to provide a method of using the cell permeable peptide for transporting the cell-impermeable material.

Another object of the present invention is to provide a conjugate in which a bioactive peptide or protein is bound to the cell permeable peptide.

Another object of the present invention is to provide uses of a conjugate in which a bioactive peptide is bound to the cell permeable peptide for preventing or treating bone diseases or autoimmune diseases.

Another object of the present invention is to provide a pharmaceutical composition including a conjugate in which a bioactive peptide is bound to the cell permeable peptide and a pharmaceutically acceptable carrier.

Another object of the present invention is to provide a pharmaceutical composition for preventing or treating bone diseases or autoimmune diseases including a conjugate in which a bioactive peptide is bound to the cell permeable peptide and a pharmaceutically acceptable carrier.

Another object of the present invention is to provide a method for preventing or treating bone diseases or autoimmune diseases including administering a pharmaceutical composition including a conjugate in which a bioactive peptide is bound to the cell permeable peptide and a pharmaceutically acceptable carrier to an individual.

To achieve the above object, the present invention provides a human-derived cell permeable peptide consisting of 5 to 15 amino acids sequence and containing at least one amino acid selected from a group consisting of arginine, lysine, and histidine at a content of 70 to 80%.

According to another aspect of the present invention, there is provided uses of the cell permeable peptide for transporting a cell impermeable material.

According to still another aspect of the present invention, there is provided a method of using the cell permeable peptide for transporting a cell impermeable material.

According to still another aspect of the present invention, there is provided a conjugate in which a bioactive peptide or protein is bound to the cell permeable peptide.

According to still another aspect of the present invention, there is provided uses of a conjugate in which a bioactive peptide or protein is bound to the cell permeable peptide for preventing or treating diseases.

According to still another aspect of the present invention, there is provided uses of a conjugate in which a bioactive peptide or protein is bound to the cell permeable peptide for preventing or treating bone diseases or autoimmune diseases.

According to still another aspect of the present invention, there is provided a pharmaceutical composition for preventing or treating bone diseases including a conjugate in which a bioactive peptide having a bone differentiation inducing sequence or a bone regeneration inducing sequence is bound to the cell permeable peptide and a pharmaceutically acceptable carrier.

According to still another aspect of the present invention, there is provided a pharmaceutical composition for preventing or treating autoimmune diseases including a conjugate in which a bioactive peptide having an anti-inflammatory function is bound to the cell permeable peptide and a pharmaceutically acceptable carrier.

According to still another aspect of the present invention, there is provided a method for preventing or treating bone diseases or autoimmune diseases including administering a pharmaceutical composition including a conjugate in which a bioactive peptide is bound to the cell permeable peptide and a pharmaceutically acceptable carrier to an individual.

BRIEF DESCRIPTION OF DRAWINGS

FIG. 2A is a sensor-gram showing affinities of the conjugate and the comparative domain to Smurf1 by BIACORE®, FIG. 2B shows results obtained by confirming the biological activity of materials treated with the conjugate and the comparative domain against intracellular decomposition action of Smad1/5/8 using the immunoprecipitation method, and FIGS. 2C and 2D show results confirming the affinity of the material treated with the conjugate and the comparative domain to Smurf1 and affinities according to the concentration by slot blotting.

FIGS. 3A to 3C are results obtained by measuring permeability of a fluorescence-labeled cell permeable peptide-bioactive peptide (bone differentiation inducing sequence) conjugate according to the present invention and a comparative domain, wherein FIG. 3A is a confocal scanning microscope photograph, and FIG. 3B is a graph showing results measured using flow cytometry.

FIG. 4B is a graph showing results obtained by a quantitative real-time polymerase chain reaction (quantitative real-time PCR) with respect to ALP, OCN, and RUNX2, which are bone differentiation markers. FIG. 4C is a photograph of reactants of FIG. 4B stained with EtBr and photographed under UV light using an electrophoresis method, and FIG. 4D is a result showing a difference in the cell differentiation abilities of the cell permeable peptide-bioactive peptide (bone differentiation inducing sequence) conjugate according to the present invention and the comparative domains by separating cytoplasm and a nucleus from each other and using a protein playing an important role in signal transduction pathways involved in bone differentiation by a western blotting assay method.

DETAILED DESCRIPTION OF THE INVENTION AND THE DETAILED EMBODIMENTS

Figure 1:
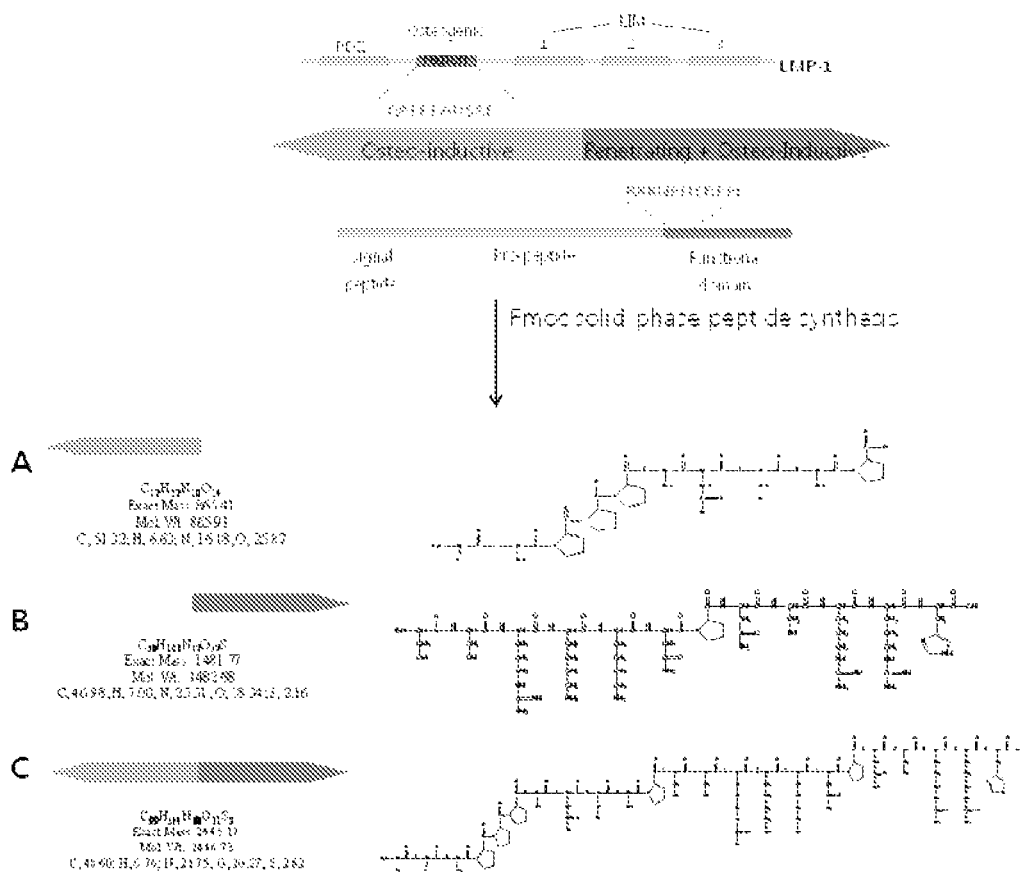
FIG. 1 is a view schematically showing origins and chemical structures of a cell permeable peptide-bioactive peptide (bone differentiation inducing sequence) conjugate according to the present invention and comparative domains.

Unless otherwise defined herein, technical and scientific terms used in the present specification have the same meanings as those understood by specialists in the skilled art to which the present invention pertains. Generally, nomenclature used in the present specification is well known and commonly used in the art.

The present invention relates to an intracellular transduction method of producing a cell permeable peptide to allow an impermeable bioactive material bound thereto such as peptide, drug, or the like, to permeate into only cells, wherein the impermeable bioactive material to be introduced such as the peptide, the drug, or the like, is chemically bound to the cell permeable peptide and treated in an aqueous state in vivo and in vitro, such that the impermeable bioactive material may rapidly and safely permeate into the cell. That is, the impermeable bioactive material may be directly introduced into the cell without performing an endocytosis process, which is an existing absorption process into cells.

In one general aspect, the present invention relates to a human-derived cell permeable peptide consisting of 5 to 15 amino acids sequence and containing at least one amino acid selected from a group consisting of arginine, lysine, and histidine at a content of 70 to 80%.

In the present invention, the cell permeable peptide may be selected from a group consisting of H4S (SEQ ID No. 1: SSRKKNPNCRRH), H4Q (SEQ ID No. 2: QRARKKNKN-CRRH), HBD-3P (SEQ ID No. 3: CSTRGRKCCRRKK), H2 (SEQ ID No. 4: HKREKRQAKHKQRKR), H3 (SEQ ID No. 5: KSKNKKKQRKGPHRK), H3B (SEQ ID No. 6: KPRPGRKDRRKK), H4-1 (SEQ ID No. 7: RRRRAKRSP-KHHS), H6 (SEQ ID No. 8: SRRRQQSRNR), H8 (SEQ ID No. 9: RAVRPLRRRQPKKS), H4C (SEQ ID No. 10: CSS-RKKNPNCRRH), H5C (SEQ ID No. 11: CSS-RKKNKNCPRRH), and H6C (SEQ ID No. 12: CSSRKKN-PNCPRRH).

The H4Q is a human BMP-4 derived peptide, HBD-3P is a human beta defensin derived peptide, H2 is a human BMP-2 derived peptide, H3 and H3B are human BMP-3 derived peptides, H4-1 is a partially modified human BMP-4 derived peptide, H6 is a human BMP-6 derived peptide, and H8 is a human BMP-8 derived peptide.

In another aspect, the present invention relates to a conjugate in which a bioactive peptide or protein is bound to the cell permeable peptide.

In the present invention, the cell permeable peptide-bioactive peptide conjugate may be chemically synthesized using a peptide synthesizer. That is, the cell permeable peptide-bioactive peptide conjugate may be synthesized by sequentially chemically synthesizing the bone differentiation inducing sequence or a bioactive domain in a C terminal region of a protein transduction domain (PTD) having cell permeability in a sequence of 'an N-terminal, the PTD domain, bone differentiation inducing sequence or the bioactive domain, and the C terminal' or 'the N-terminal, the bone differentiation inducing sequence or the bioactive domain, the PTD, and the C-terminal. The bioactive domain, which is a material regulating gene expression and physiological functions in vitro or in vivo in addition to inducing bone differentiation, may serve to correct an abnormal state due to deficiency or excessive secretion of a material involved in regulating functions in vivo and be a L-type domain or D-type domain in consideration of stability in vivo. In the present invention, the term "bioactive domain" is used as a meaning to include bone differentiation inducing sequences, bone regeneration inducing sequences, and anti-inflammatory functional sequences and may be selected from a group consisting of the SEQ ID No. 13 (GAP-PPADSAP), the SEQ ID No. 14 (PPGY), the SEQ ID No. 15 (PPAY), which are the bone differentiation or regeneration inducing sequence, and the SEQ ID No. 16 (anticare peptide: TRGRKCCRRKK), which is the anti-inflammatory functional sequence. In addition, the bioactive inducing sequence may be a peptide having an anti-inflammatory or antibiotic functional sequence or a cell attachment inducing sequence.

In the present invention, the cell permeable peptide may contain at least one amino acid selected from a group consisting of arginine, lysine, and histidine at a content of 70 to 80%, wherein the amino acid configuring the cell permeable peptide may be an L-type or D-type amino acid in consideration of stability in vivo.

As the cell permeable peptide-bioactive peptide conjugate according to the present invention, which is the PTD having cell permeability, other cationic PTD peptides, that is, peptides containing arginine, lysine, or histidine at a content of 70 to 80% or more, may be preferably used except for H4S (SEQ ID No. 1: SSRKKNPNCRRH), which is a transduction domain discovered by the present inventors. Preferably, H4Q (SEQ ID No. 2: QRARKKNKNCRRH), HBD-3P (SEQ ID No. 3: CSTRGRKCCRRKK), H2 (SEQ ID No. 4: HKREKRQAKHKQRKR), H3 (SEQ ID No. 5: KSKNKKKQRKGPHRK), H3B (SEQ ID No. 6: KPRPGRKDRRKK), H4-1 (SEQ ID No. 7: RRRRAKRSP-KHHS), H6 (SEQ ID No. 8: SRRRQQSRNR), H8 (SEQ ID No. 9: RAVRPLRRRQPKKS), H4C (SEQ ID No. 10: CSSRKKNPNCRRH), H5C (SEQ ID No. 11: CSSRKKNKNCPRRH), H6C (SEQ ID No. 12: CSSRKKNP-NCPRRH), may be used, but other peptides or peptide derivatives except for the above-mentioned peptide may also be used as long as it may permeate through the cell membrane. In addition, in a scheme similar thereto, the cell permeable peptide-bioactive peptide conjugate according to the present invention may also be produced using an existing non-human derived cell permeable domain, for example, TAT, arginine derived peptides. However, in the present invention, in order to impart bio-compatibility, the human-derived peptides are described, but it does not mean that the present invention may not be applied to the existing virus or non-human derived peptides.

The cell permeable-bioactive peptide (bone differentiation inducing sequence) conjugate according to the present invention is covalently bound to a fluorescent dye used in an optical image or contrast agent nanoparticles used in magnetic resonance image, such that the conjugate may be applied to diagnosis and treatment of bone differentiation and regeneration in cell and body. In this case, the fluorescent dye or the contrast agent nanoparticles may be covalently bound to an N or C terminal of the cell permeable-bioactive peptide (bone differentiation inducing sequence) conjugate. Preferably, cysteine may be additionally attached to the terminal of the PTD.

In addition, a complex of the cell permeable peptide-bioactive peptide (bone differentiation inducing sequence) conjugate and the fluorescent dye or the contrast agent nanoparticles may be produced by inducing chemical bonds using a cross-linking agent. In the case in which the chemical bond is induced using the cross-linking agent, the PTD peptide, that is, N terminals of the PTD have free amino groups, respectively, such that formation of the complex by the cross-linking agent may be easy. Examples of the cross-linking agent that may be used in the present invention include 1,4-bis-maleimidobutane (BMB), 1,11-bis-maleimidotetraethyleneglycol, (BM[PEO]4), 1-ethyl-3-[3-dimethyl aminopropyl]carbodiimide hydrochloride (EDC), succinimidyl-4-[N-maleimidomethylcyclohexane-1-carboxy-[6-amidocaproate]] (SMCC) and sulfo-SMCC, succimidyl 6-[3-(2-pyridyldithio)-ropionamido]hexanoate (SPDP) and sulfo-SPDP, m-maleimidobenzoyl-N-hydroxysuccinimide ester (MBS) and sulfo-MBS, succimidyl[4-(p-maleimidophenyl) butyrate] (SMPB) and sulfo-SMPB, and the like, but are not limited thereto.

In another aspect, the present invention relates to a pharmaceutical composition for preventing or treating bone diseases including a conjugate in which a bioactive peptide selected from a group consisting SEQ ID No.: 13 to SEQ ID No.: 15 is bound to the cell permeable peptide and a pharmaceutically acceptable carrier. That is, the present invention may provide a pharmaceutical composition for treating bone defects, metabolic bone diseases, or the like, wherein the bone disease is selected from a group consisting of osteoporosis, osteogenesis imperfecta, hypercalcemia, osteomalacia, Paget's disease, bone loss by cancer, and bone necrosis, and the pharmaceutical composition is formulated in an injection form.

In addition, the present invention relates to a pharmaceutical composition for preventing or treating autoimmune diseases including a conjugate in which a bioactive peptide of SEQ ID No.: 16 is bound to the cell permeable peptide and a pharmaceutically acceptable carrier, wherein the autoimmune disease is rheumatic arthritis or psoriasis, and the pharmaceutical composition is formulated in a transdermal form composition such as ointment or patch.

The present invention may provide a method for preventing or treating bone diseases or autoimmune diseases including administering a pharmaceutical composition including a conjugate in which a bioactive peptide is bound to the cell permeable peptide and a pharmaceutically acceptable carrier to an individual.

The pharmaceutical composition according to the present invention may be formulated in a form for oral administration, such as powders, granules, tablets, capsules, suspensions, emulsions, syrups, aerosols, or the like, for external application, suppository, and sterile injection solutions. As the carrier, an excipient, and a diluent contained in the composition, there are lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxybenzoate, talc, magnesium stearate, and mineral oil.

In the case in which the pharmaceutical composition is formulated, generally used diluents or excipients such as fillers, extenders, binders, wetting agents, disintegrants, surfactants, or the like, may be used. Solid formulations for oral administration includes tablets, pills, powders, granules, capsules, and the like, and may be prepared by mixing the extract with at least one excipient, for example, starch, calcium carbonate, sucrose or lactose, gelatin, or the like. Further, lubricants such as magnesium stearate or talc may be used in addition to simple excipients. Liquid formulations for oral administration include suspensions, solutions, emulsions, syrups, and the like, and various excipients such as a wetting agent, a sweetener, a flavoring agent, an aromatic piece, a preservant, or the like, as well as water and liquid paraffin that are generally used simple diluents may be contained. Formulations for parenteral administration include sterile aqueous solutions, nonaqueous solvents, suspensions, emulsions, freeze-dried formulations, and suppositories. In the nonaqueous solvent or the suspensions, propylene glycol, polyethylene glycol, vegetable oil such as olive oil, injectable esters such as ethyloleate, or the like, may be used. As a base for suppositories, witepsol, macrogol, tween 61, cacao butter, laurinum, glycerol-gelatin, or the like, may be used.

A preferable dosage of the composition of the present invention may be changed according to the state and weight of a patient, the degree of disease, the formulations, and the administration route and duration, but be appropriately selected by those in the art. However, in order to obtain a preferable effect, the composition according to the present invention may be administered at a daily dose of 0.0001 to 500 mg/kg, preferably 0.001 to 250 mg/kg. One dose may be administered once a day or divided into several to be administered. The scope of the present invention is not limited to the dose.

In the present invention, the term 'PTD' means a permeable peptide capable of permeating a drug or drug-containing particles into the cytoplasm or nucleus, or the like. The permeating peptide may covalently bind to oligonucleotide, peptide, protein, oligosaccharide, polysaccharides, nanoparticles, or the like to introduce this material into cell without requiring a separate receptor or transporter and energy.

In the present invention, the term 'bone differentiation induction' among bioactive functions means a function of inducing calcifications of extracellular matrix (ECM) using adult stem cells having a possibility of being differentiated into osteoblast cells, and changing a shape and generating bone nodule through cell differentiation, or changing cell characteristics to thereby be differentiated into a osteoblast cells. Alternatively, the 'bone differentiation induction' means a phenomenon of grafting a bone graft material, bone cells or a biocompatible supporter containing stem cell capable of being differentiated into the bone cells to induce bone regeneration in vivo, but is not limited thereto. That is, all kinds of technologies or materials that may be used for bone regeneration may be collectively referred to as the 'bone differentiation induction'.

In the present invention, the term "anti-inflammatory function" among the bioactive functions means materials capable of blocking protein inducing inflammation in cells and a technology of identifying the materials.

EXAMPLES

Hereinafter, the present invention will be described in detail through the Examples. However, these Examples are only to illustrate the present invention, and those skilled in the art will appreciate that these Examples are not to be construed as limiting a scope of the present invention.

Example 1

A peptide was synthesized by the F-moc solid phase chemical synthesis method using a peptide synthesizer, so as to contain GAPPPADSAP (SEQ ID NO: 7) as a bone differentiation inducing sequence derived from LMP1, and H4S (SSRKKNPNCRRH, SEQ ID NO: 1) as a PTD, sequentially from the N-terminus thereof (See FIG. 1). That is, the Rink resin (0.075 mmol/g, 100~200 mesh, 1% DVB crosslinking) to which Fmoc-(9-Fluorenylmethoxycarbonyl) binds was used as a blocking group. 50 mg of the Rink resin was introduced into the synthesizer, and then subjected to swelling using DMF. Then, a 20% piperidine/DMF solution was used to remove the Fmoc-group. A 0.5M amino acid solution (solvent: DMF), a 1.0M DIPEA solution (solvent: DMF&NMP), and a 0.5M HBTU solution (solvent: DMF) were sequentially introduced in 5, 10, and 5 equivalents, respectively, from the C-terminal of the peptide, followed by reaction for 1-2 hours under the nitrogen atmosphere. Whenever the deprotection and coupling were ended, washing with DMF and NMP was carried out twice. Even after the final amino acid was coupled, deprotection was carried out to remove the Fmoc-group.

The ninhydrin test was used to confirm the synthesis. The resin tested and completely synthesized was dried over THF or DCM. Then, the TFA cleavage cocktail was input at a ratio of 20 ml per 1 g of resin, and then shaked for 3 hours, followed by filtering, to isolate the resin and the cocktail in which peptide was dissolved. The filtrate solution was evaporated by using a rotary evaporator and then cold ether was input, or a large amount of cold ether was directly input into the TFA cocktail solution in which peptide was dissolved to crystallize the peptide in a solid phase, which was then isolated by centrifugation. Here, the TFA cocktail was completely removed by several times of washing with ether and centrifugation. The thus obtained peptide was dissolved in distilled water, and then freeze-dried.

(SEQ ID No: 17)
NH$_2$-GAPPPADSAP-SSRKKNPNCRRH-C-COONH$_2$

After the synthesized peptide was cleaved from the resin, washed, and then freeze-dried, it was isolated and purified by liquid chromatography. The purified peptide was subjected to MALDI analysis, to confirm the molecular weight thereof.

Comparative Example 1

H4S(SSRKKNPNCRRH; SEQ ID No.: 1) as PTD

The peptide was synthesized by the F-moc solid phase chemical synthesis method using a peptide synthesizer.

Comparative Example 2

Bone Differentiation Inducing Sequence ((GAPPPADSAP; SEQ ID No.: 13) Derived form LMP1

The peptide was synthesized by the F-moc solid phase chemical synthesis method using a peptide synthesizer.

Example 2

Confirmation of Affinity Between Cell Permeable Peptide-Bone Differentiation Inducing Sequence Conjugate and Smurf1

2-1: Confirmation of Affinity Between Cell Permeable Peptide-Bone Differentiation Inducing Sequence Conjugate and Smurf1 Using Surface Plasmon Resonance Detection Assay Method In order to confirm the affinity between cell permeable peptide-bone differentiation inducing sequence conjugate and Smurf1 by a chemical method, a human-derived Smurf1 protein acting as a ligand in the present experiment was purchased from Origene Technologies (Rockville, Md., USA). The protein (100 mg/ml) was coupled to a gold coated surface of a CM5 chip (BIACORE AB, Sweden) on which amino groups are bounded using an EDC/NHS kit (BIACORE AB, Sweden). (Instead of this experimental method, 'Immobilization' integrated into the BIACORE® T100 (BIACORE AB, Sweden) software used by the present inventors may be used). In this case, in order to find a suitable pH condition at which the protein may bind to the amino group in the CM5 chip, a method called 'pH scouting' was performed, thereby finding a pH condition. As a method of 'pH scouting', a method integrated in the BIACORE® T100 (BIACORE AB, Sweden) software used by the present inventors may be used. Under the pH condition derived by the above-mentioned method, after binding the ligand, the affinity was measured while flowing 10 mM analytes (the cell permeable peptide-bone differentiation inducing sequence conjugate synthesized in Example 1, the cell permeable peptide of Comparative Example 1 used as a negative control group, and the bone differentiation inducing sequence of Comparative Example 2 as a positive control group) onto the CM5 chip, respectively. (Instead of this experimental method, 'binding analysis' integrated in the BIACORE® T100 (BIACORE AB, Sweden) software used by the present inventors may be used).

Figure 2:
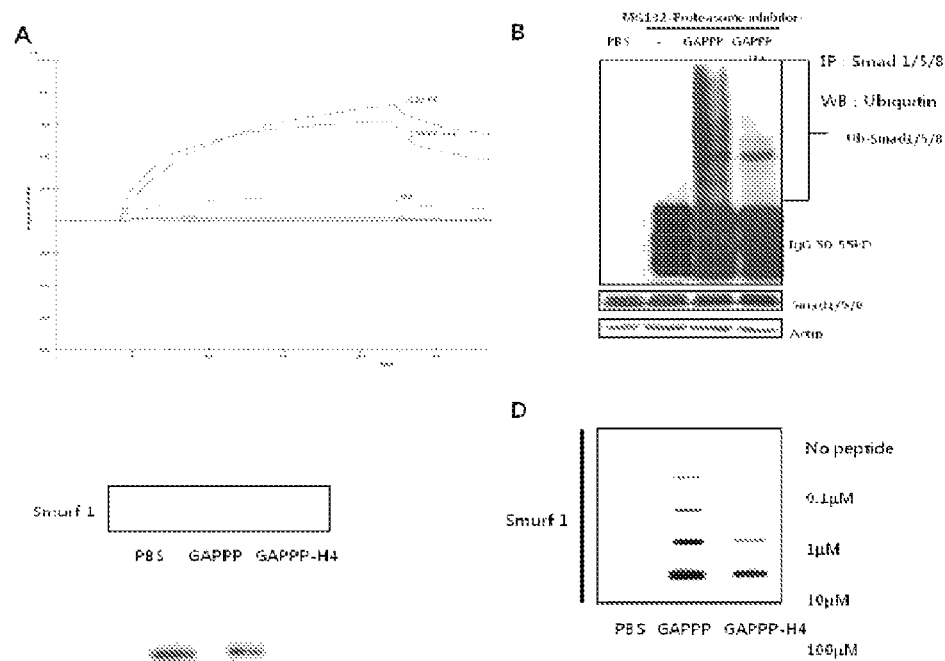
FIGS. 2A to 2D are views showing accuracy of synthesis of the cell permeable peptide-bioactive peptide (bone differentiation inducing sequence) conjugate according to the present invention and the comparative domains. A bioactivity (affinity) of the conjugate was observed using a chemical and molecular biological method.

As a result, as shown in FIG. 2A, the affinity of Comparative Example 2 (GAPPPADSAP) which is a site binding to a WW domain of a Smurf1 protein sequence and has bone differentiation activity, to Smurf1 was 750 RU (Resonance Unit; unit for measuring affinity), the affinity of the cell permeable peptide-bone differentiation inducing sequence conjugate synthesized in Example 1 was 600 RU, and the affinity of the cell permeable peptide of Comparative Example 1 used as the negative control group was 100 RU. The result showed that the cell permeable peptide-bone differentiation inducing sequence conjugate has a bone differentiation inducing sequence, and significant damage does not occur in the bioactive sequence (site binding to Smurf1 to exhibit the function in vivo) during a synthesis process.

2-2: Confirmation of Affinity Between Cell Permeable Peptide-Bone Differentiation Inducing Sequence Conjugate and Smurf1 Using Immuno-Precipitation Method In order to confirm presence or absence of the active site of the cell permeable peptide-bone differentiation inducing sequence conjugate synthesized by the method in Example 1 for binding to Smurf1, an immuno-precipitation method and a western blot assay method were used. The present experimental method is applied in order to confirm that the cell permeable peptide-bone differentiation inducing sequence conjugate synthesized by the method in Example 1 may suppress a bioactivity of Smurf1 decomposing Smd1/5/8 as one of the E3 ligases playing a role in ubiquitin ligation.

1×106 human mesenchymal stem cells (hMSC) used as a model cell in the present experiment were plated in each dish and then cultured in a general medium for 20 hours (overnight incubation). Then the cells was cultured in an hMSC basal medium (MSCBM™, LONZA, USA) containing 0.5% fetal bovine serum (FBS, GIBCO, USA) for 20 hours (overnight starvation). After overnight starvation in 0.5% MSCBM™, 10 mM MG132 (MG132; proteasome inhibitor, Merck, USA) was added to the same medium to allow the cells to be pre-treated for 2 hours. Thereafter, the cell permeable peptide-bone differentiation inducing sequence conjugate synthesized by the method in Example 1 and peptides of Comparative Examples 1 and 2 were injected into each dish at a concentration of 10 mM, respectively, and cultured for 1 hour 30 minutes.

hMSCs synthesized in Example 1 and Comparative Example 2 were lysed using a cell lysis buffer (1% triton X-100, 150 mM NaCl, 50 mM Tris-Cl (pH 7.5), 0.1% SDS, 1% NP-40, 1 mM PMSF). In order to obtain a supernatant of protein from cell lysate, the cell lysate was centrifuged at 12,000 rpm (4° C., 10 minutes). The supernatant was moved to a new tube, and in order to perform the immuno-precipitation method, the cell lysate was treated with Smad1/5/8 antibody (5 µg) to thereby conduct a reaction at 4° C. for 20 minutes. Then, protein A/G-agarose beads were added to conduct a reaction at 4° C. for 4 hours. The beads were washed with PBS containing 1 mM DTT 3 times and then boiled with 2× protein loading dye (25% SDS, 62.5 mM Tris-HCl (pH 6.8), 25% Gylcerol, and 0.01% Bromophenol Blue) for 5 minutes. The samples were isolated on electrophoresis using SDS-PAGE.

In order to perform the western blot assay, the binding proteins isolated by the SDS-PAGE were moved onto a nitrocellulose membrane (NC membrane). Blocking was performed on the NC membrane onto which the proteins were moved in 5% skim-milk at room temperature for 1 hour. The NC membrane was washed with a TBST solution for 10 minutes three times. The washed NC membrane was reacted with 1 µg of the ubiquitin antibody used as primary antibodies at room temperature for 4 hours. Next, the NC membrane was washed with a TB ST solution for 10 minutes three times and then reacted with secondary antibodies having horse radish peroxidase (HRP) attached thereto at room temperature for 1 hour. The NC membrane was washed with a TBST solution for 10 minutes three times and exposed to X-ray to film using an enhanced chemo-luminal (ECL) in a dark room (TBST: a 1 L of TBST solution was prepared using 8.8 g of NaCl, 0.2 g of KCl, 3 g of Tris base (pH 7.4), and 0.05% Tween® 20.

As a result, as shown in FIG. 2B, it may be appreciated that the ubiquitin antibodies was detected overall while exhibiting a tailing phenomenon in a lane in a group treated with only MG132 due to a phenomenon that ubiquitin binding to the protein (in the present experiment, Smad1/5/8) was not decomposed through the proteasome inhibitor. This phenomenon was equally indicated in the group treated with the bone differentiation inducing sequence synthesized in Comparative Example 2, but it was confirmed in the rightmost lane that ubiquitination of Smad1/5/8 was suppressed in the group treated with the cell permeable peptide-bone differentiation inducing sequence conjugate, The result estimated that the conjugate may inhibit decomposition of Smad1/5/8 to promote bone tissue differentiation and bone regeneration by penetrating into cell to bind to the WW domain of Smurf1 was obtained. Therefore, accuracy of the synthesis processes of the conjugate and the bone differentiation inducing sequence (Comparative Example 2) were confirmed.

2-3: Confirmation of Affinity Between Cell Permeable Peptide-Bone Differentiation Inducing Sequence Conjugate and Smurf1 Using Slot-Blot Assay Method In order to confirm presence or absence of the active site of the cell permeable peptide-bone differentiation inducing sequence conjugate synthesized by the method in Example 1 for binding to Smurf1 and binding degrees according to the concentration, a slot blot assay were used. This experimental method is a molecular biological method of positioning a protein on a membrane and sucking the protein in the other side to strongly attach the protein on a surface of the membrane, directly positioning a material to be confirm an interaction with the attached protein and culturing for a predetermine time to induce the binding, and blotting them using antibodies to confirm the interaction (affinity) between the protein and the material through a difference of each Dot.

1 µg of human-derived Smurf1 protein was input 20 ml per well using a slot blot device (Hoefer, Pharmacia Biotech, USA) and blotted on a predetermined position on a nitrocellulose membrane (2 µm, Pall, USA) in a vacuum state. After blotting, the nitrocellulose membrane was blocked with phosphate buffer solution containing 0.5% Tween® 20 at room temperature for 30 minutes, and then completely dried. The domains synthesized in Example 1 and Comparative Examples 1 and 2 was biotinylated using EZ-Link Sulfo-NHS-Biotin (Pierce Biotechnology, USA) according to an experimental method of the manufacturer, and unbound byproduct was removed through ultrafiltration, which is a membrane filtration method using a pressure difference. Then, the resultant was freeze-dried. The freeze-dried domains were dissolved in distilled water, input at a volume of 200 ml into wells of a culture tray at concentrations of 0.1, 1, 10, and 100 mM, and cultured at 4° C. for 20 hours, respectively. After reaction for 20 hours, the domains was blocked with the phosphate buffer solution containing 0.5% Tween® 20 at room temperature for 30 minutes, and then reacted with Extravidin® (a secondary antibody) (SIGMA, USA) at room temperature for 1 hour. The reactant was washed with TBST for 10 minutes 3 times and exposed to X-ray film using the enhanced chemo-luminal (ECL) in a darkroom.

As a result, as shown in FIGS. 2C and 2D, it may be confirmed through this experiment that the Smurf1 protein and the domain of Comparative Example 2 used as the positive control group were bound to each other to thereby be detected as dot as shown in FIG. 2C, and a dot was confirmed on a portion at which binding of the Smurf1 protein and the cell permeable peptide-bone differentiation inducing sequence conjugate was induced. In FIG. 2D, it was confirmed that when the cell permeable peptide-bone differentiation inducing sequence conjugate or the bone differentiation inducing sequence were cultured with Smurf1 at each concentration, in the case of the bone differentiation inducing sequence (Comparative Example 2), a dot size was increased as the concentration was increased from 0.1 mM to 100 mM, and in the case of the cell permeable peptide-bone differentiation inducing sequence conjugate, an increase of a dot size began at a concentration of 10 mM. This result means that two materials (the conjugates obtained in Example 1 and Comparative Example 2 and the Smurf1 protein) may bind to each other in vitro, and the binding may be increased according to the concentration.

Example 3

Measurement of Cell Permeability of Cell Permeable Peptide-Bone Differentiation Inducing Sequence Conjugate In Vitro 3-1: Synthesis of Fluorescence Labeled Cell Permeable Peptide-Bone Differentiation Inducing Sequence Conjugate The domains synthesized in Example 1 and Comparative Examples 1 and 2 were labeled with a fluorescent material in order to measure cell permeability. 10 equivalents of fluorescein isothiocyanate (FITC) was bound to N-terminals of the synthesized domains by using triethylamine (1 ml per 1 g of resin). The synthesis of the peptide was confirmed by measuring the molecular weight thereof through MALDI-TOF.

The resultant was analyzed and purified using reverse phase liquid chromatography. Analysis was performed using a C18 column having a diameter of 4.6 mm, and 0.1% TFA/$H_2O$ and 0.092% TFA/acetonitrile (0 to 60%) were flowed at a flow rate of 1 ml/min for 30 minutes. In this case, a wavelength of an UV detector was 220 nm. In the case of the fluorescent material labeled peptide, a fluorescence detector (Ex: 493.5 nm, Em: 460 nm) was used, and a wavelength of the UV detector was 220 nm.

Purification was performed using a column having a diameter of 2.2 cm at a flow rate of 20 ml/min at a condition at which the solvent and the detection wave length were the same as described above. Only pure peptide was isolated and collected to evaporate the solvent therefrom using a rotary evaporator and then freeze-dried.

3-2: Fluorescence Imaging Measurement of Cell Permeability of Cell Permeable Peptide-Bone Differentiation Inducing Sequence Conjugate In order to measure the cell permeability of the cell permeable peptide-bone differentiation inducing sequence conjugate, after sterile slide glass was input in a 6-well plate and $2\times10^4$ human mesenchymal stem cells (hMSC) were plated in each well, the cells were cultured in a general medium for 20 hours (overnight incubation). Then the cells was cultured in an hMSC basal medium (MSCBM, LONZA, USA) containing 0.5% fetal bovine serum (FBS, GIBCO, USA) for 20 hours (overnight starvation). 100 mM fluorescence labeled cell permeable peptide-bone differentiation inducing sequence conjugate and 100 mM fluorescence labeled bone differentiation inducing sequence that were obtained by binding FITC (SIGMA, USA) N-terminals of the cell permeable peptide-bone differentiation inducing sequence conjugate synthesized by the method in Example 1 and the domain in Comparative Example 2 to synthesize the fluorescence label conjugate and fluorescence label domain, followed by isolation and purification, were injected into each well and washed with phosphate buffer solution (PBS) two times after 20 minutes and 80 minutes of injection. The resultants was observed using a confocal scanning microscope (IX 70, Olympus Co., Tokyo, Japan).

Figure 3:
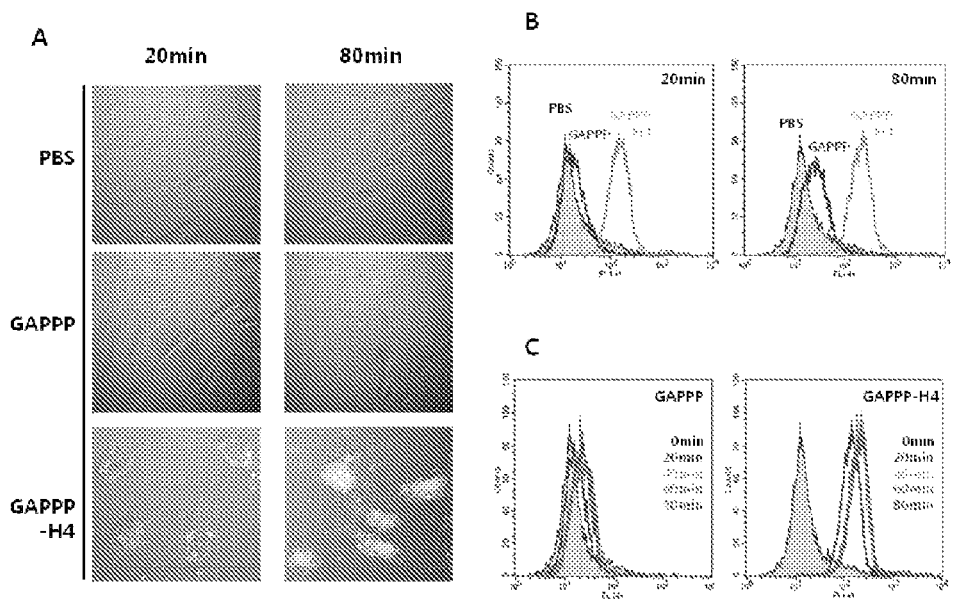

As a result, as shown in FIG. 3A, when the cells were treated with the cell permeable peptide-bone differentiation inducing sequence conjugate of Example 1 and the bone differentiation inducing sequence of Comparative Example 2 to which FITC (green) was bound, the bone differentiation inducing sequence did not permeate into cell. However, in the case of the cell permeable peptide-bone differentiation inducing sequence conjugate of Example 1 in which the PTD sequence of Comparative Example 1 were contained, fluorescent particles were observed in the cytoplasm after 20 minutes of treatment and clearly observed in the cytoplasm and nucleus after 80 minutes of treatment. Therefore, it may be appreciated that the cell permeability was increased dependently on the time (provided that observation was performed within 80 minutes) due to the PTD sequence contained in the cell permeable peptide-bone differentiation inducing sequence.

Figure 7:
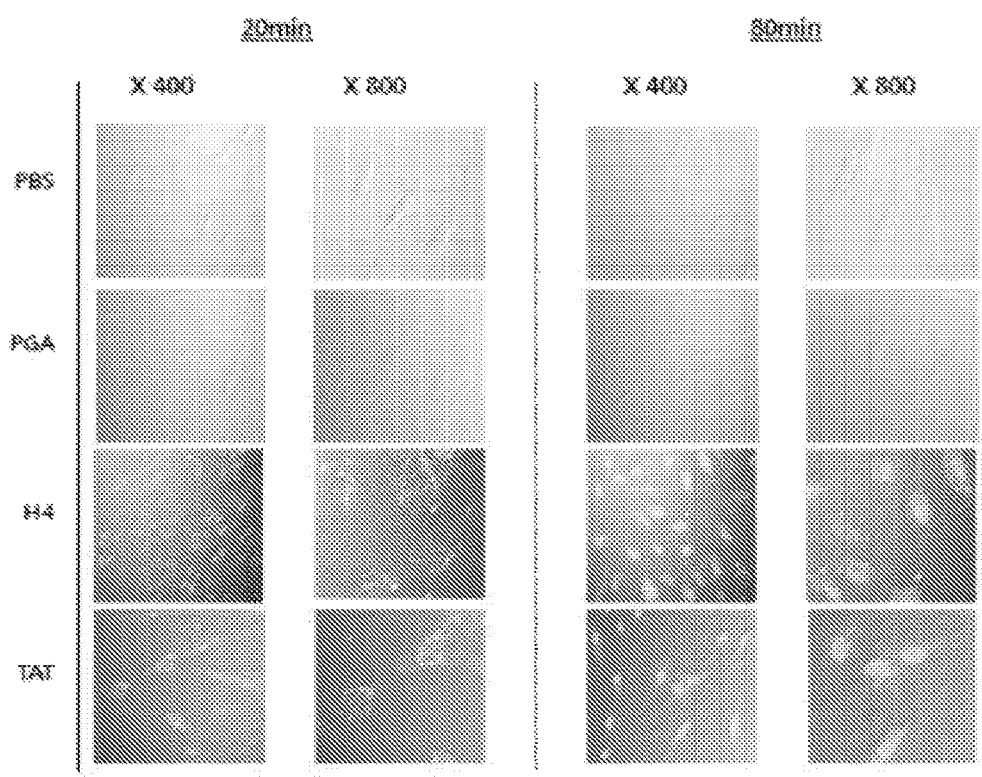
FIG. 7 is photographs comparing cell permeability of a separate fluorescence-labeled cell permeable peptide according to the present invention and the existing well known cell permeable peptide TAT with each other. A culturing time was 20 and 80 minutes, TAT was used as a positive control group and poly-glutamic acid (PGA, CGGGEEEEEEEEEEE) was used as a negative control group, and observation was conducted using a confocal scanning microscope.
Figure 8:
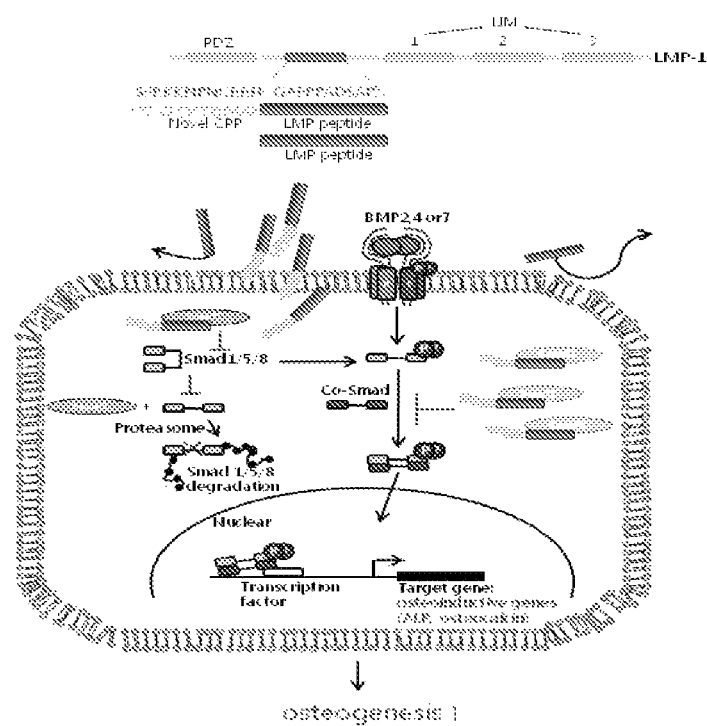
FIG. 8 is a view showing an influence of the cell permeable peptide-bioactive peptide (bond differentiation inducing sequence) conjugate according to the present invention on the signal transduction pathways involved in the bone differentiation when human mesenchymal stem cells are treated with the conjugate.

In addition, as shown in FIG. 7, when groups using TAT (existing virus derived cationic material known as a strong cell permeable peptide) and the H4S of Comparative Example 1, which is the PTD of the present invention, were compared with each other, fluorescent materials uniformly present in cytoplasm were observed after 20 minutes in both of the groups, and fluorescent materials densely present up to in nucleus were confirmed after 80 minutes in both of the groups. Therefore, it was found that a cell permeation rate and accumulation state of H4S, which is a main material of the present invention, were similar to those of TAT in hMSC.

3-3: Measurement of Cell Permeability of Cell Permeable Peptide-Bone Differentiation Inducing Sequence Conjugate Using Flow Cytometry In order to quantitatively confirm the cell permeability and cell permeation degree of fluorescence labeled magnetic nanoparticle conjugates, after $1\times10^5$ human mesenchymal stem cells (hMSC) were plated in each well of 6-well plate, the cells were cultured in a general medium for 20 hours (overnight incubation). Then the cells was cultured in an hMSC basal medium (MSCBM, LONZA, USA) containing 0.5% fetal bovine serum (FBS, GIBCO, USA) for 20 hours (overnight starvation). 100 mM fluorescence labeled cell permeable peptide-bone differentiation inducing sequence conjugate and 100 mM fluorescence labeled bone differentiation inducing sequence that were obtained by binding FITC (SIGMA, USA) N-terminals of the cell permeable peptide-bone differentiation inducing sequence conjugate synthesized by the method in Example 1 and the domain in Comparative Example 2 to synthesize the fluorescence label conjugate and fluorescence label domain, followed by isolation and purification, were injected into each well and washed with the phosphate buffer solution (PBS) two times after 20, 40, 60, and 80 minutes of injection. The cells were isolated from the well using 0.25% trypsin, and a process of washing the cells with the phosphate buffer solution (PBS) and isolating t supernatant using centrifugation were performed two times, thereby removing the extracellular FITC. After 300 ml of phosphate buffer solution (PBS) was added thereto to float the cells, the cells were observed FL-1 (488 nm) using a FACSCalibur (BD, USA).

As a result, as shown in FIG. 3B, when the cells were treated with the cell permeable peptide-bone differentiation inducing sequence conjugate of Example 1 and the bone differentiation inducing sequence of Comparative Example 2 to which FITC (green) was bound, the bone differentiation inducing sequence did not permeate into cell. However, in the case of the cell permeable peptide-bone differentiation inducing sequence conjugate of Example 1 in which the PTD sequence of Comparative Example 1 were contained, fluorescence intensity was relatively increased 10 times or more, such that it may be appreciated that the cell permeable peptide-bone differentiation inducing sequence conjugate has cell permeability.

Example 4

Determination on In Vitro Cell Differentiation Ability of Cell Permeable Peptide-Bone Differentiation Inducing Sequence Conjugate 4-1: Determination on Cell Differentiation Ability of Cell Permeable Peptide-Bone Differentiation Inducing Sequence Conjugate Using Alizarin Red S Staining In order to confirm cell differentiation ability of the cell permeable peptide-bone differentiation inducing sequence conjugate by the amount of phosphorylated calcium, human mesenchymal stem cells (hMSC) were seeded in a 24-well plate at $1\times10^3$/well, and then treated with the cell permeable peptide-bone differentiation inducing sequence conjugate synthesized from Example 1 and the bone differentiation inducing sequence of Comparative Example 2 of 10 mM for each, and then incubated in a hard tissue-forming medium for 14 days. The hard tissue-forming medium contained an MSCBM medium containing 15% FBS (fetal bovine serum), 50 mg/Ml of L-ascorbic acid, $10^{-7}$ M dexamethasone, 1% antibiotic-antimycotic solution, and 10 mM beta-glycerol phosphate. After completion of the incubation, the medium was removed, and then the cells were washed with phosphate buffer solution (PBS) twice. The cells were fixed using 90% ethanol at 4° C. for 15 minutes, followed by washing with distilled water twice, and then stained with 2% Alizarin red S Solution (pH 4.2; Alizarin red S powder, Junsei, JAPAN).

Figure 4:
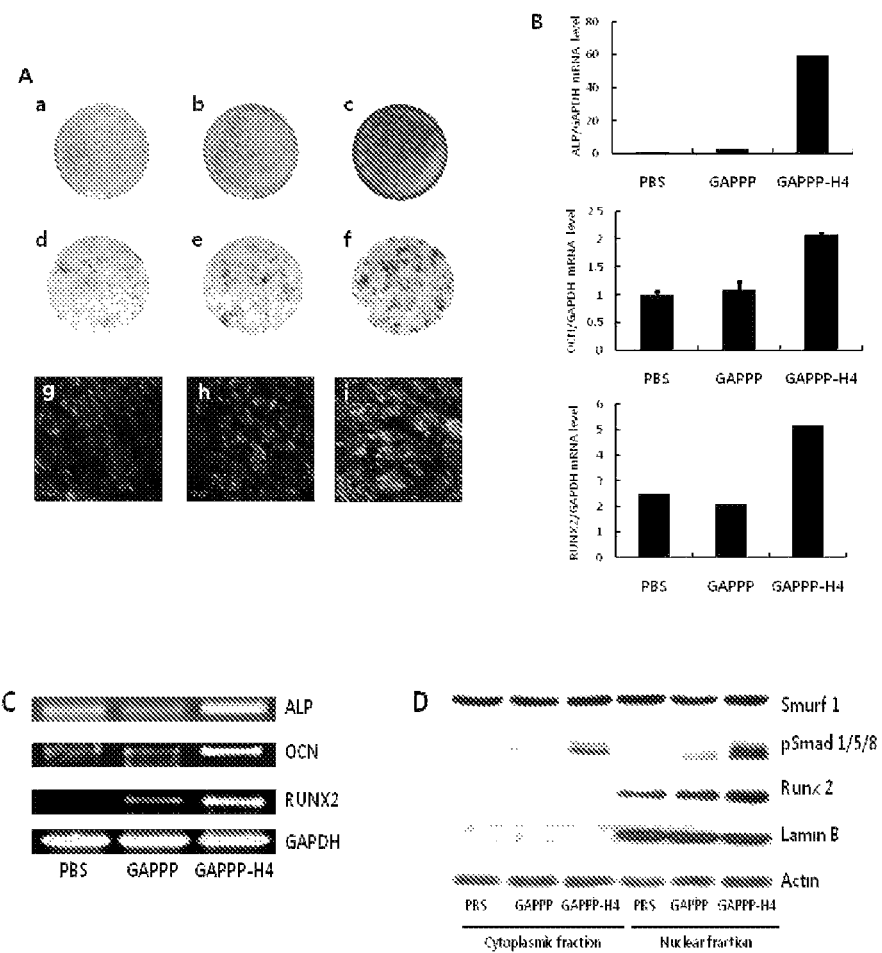
FIGS. 4A to 4D are results obtained by observing intracellular differentiation abilities of the cell permeable peptide-bioactive peptide (bone differentiation inducing sequence) conjugate according to the present invention and comparative domains. (a), (b), and (c) of FIG. 4A are groups stained with alizarin red S staining (d), (e), and (f) are groups stained with alkaline phosphatase, and (g), (h), and (i) are groups stained with Calcein. In addition, (a), (d), and (g) are groups treated with PBS, (b), (e), and (h) are groups treated with the bone differentiation inducing sequence, and (c), (f), and (i) are groups treated with the cell permeable peptide-bone differentiation inducing sequence conjugate. Each of the groups was observed using an optical microscope and a confocal scanning microscope.

As a result, as shown in FIG. 4 (A: a, b, and c), when treated with the cell permeable peptide-bone differentiation inducing sequence conjugate of Example 1 and the bone differentiation inducing sequence of Comparative Example 2, the differentiation into the osteoblast was not remarkably increased even after 14 days of incubation in the group treated with the bone differentiation inducing sequence (b) that fails in intracellular penetration as compared with the group treated with only PBS (a). Whereas, the group treated with the cell permeable peptide-bone differentiation inducing sequence conjugate (c) exhibited a relatively strong staining degree of phosphorylated calcium, and thus confirmed the cell differentiation ability of the cell permeable peptide-bone differentiation inducing sequence conjugate.

4-2: Determination on Cell Differentiation Ability of Cell Permeable Peptide-Bone Differentiation Inducing Sequence Conjugate Using Alkaline Phosphate (ALP) Staining In order to detect alkaline phosphate (ALP), which is a label material shown at the initial stage of bone differentiation, for cell differentiation ability of the cell permeable peptide-bone differentiation inducing sequence conjugate, human mesenchymal stem cells (hMSC) were seeded in a 24-well plate at $1\times10^3$/well, and then treated with the cell permeable peptide-bone differentiation inducing sequence conjugate synthesized from Example 1 and the bone differentiation inducing sequence of Comparative Example 2 of 10 mM for each, and then incubated in a hard tissue forming medium for 14 days. The hard tissue-forming medium contained an MSCBM medium containing 15% FBS (fetal bovine serum), 50 mg/Ml of L-ascorbic acid, $10^{-7}$ M dexamethasone, 1% antibiotic-antimycotic solution, and 10 mM beta-glycerol phosphate. After completion of the incubation, the medium was removed, and then the cells were washed with phosphate buffer solution (PBS) twice. The cells were fixed with 10% NBF at room temperature for 20 minutes, and then washed with a phosphate buffer solution (PBS) twice. Then, staining was conducted using the Alkaline phosphatase detection kit (Millipore, USA) by the experiment method recommended by the manufacture.

As a result, as shown in FIG. 4 (A: d, e, and f), when treated with the cell permeable peptide-bone differentiation inducing sequence conjugate of Example 1 and the bone differentiation inducing sequence of Comparative Example 2, the differentiation into osteoblast was not remarkably increased even after 14 days of the incubation in the group treated with the bone differentiation inducing sequence (e) that fails in intracellular penetration as compared with the group treated with only PBS (d). Whereas, the group treated with the cell permeable peptide-bone differentiation inducing sequence conjugate (f) exhibited a relatively strong staining degree of alkaline phosphatase, and thus confirmed the cell differentiation ability of the cell permeable peptide-bone differentiation inducing sequence conjugate.

4-3: Determination on Cell Differentiation Ability of Cell Permeable Peptide-Bone Differentiation Inducing Sequence Conjugate Using Calcein Staining In order to confirm cell differentiation ability of the cell permeable peptide-bone differentiation inducing sequence conjugate, human mesenchymal stem cells (hMSC) were seeded in each well of a 4-well chamber slide at $5\times10^3$/well, and then incubated in a general medium for 20 hours (overnight) for cell stabilization. The cells were treated with the cell permeable peptide-bone differentiation inducing sequence conjugate synthesized from Example 1 and the bone differentiation inducing sequence of Comparative Example 2 of 10 mM for each, and then incubated in a hard tissue forming medium containing calcein (calcium staining, green) for 14 days. The composition of the hard tissue-forming medium consisted of an MSCBM medium containing 15% FBS (fetal bovine serum), 50 mg/Ml of L-ascorbic acid, $10^{-7}$ M dexamethasone, 1% antibiotic-antimycotic solution, and 10 mM beta-glycerol phosphate. After completion of the incubation, the medium was removed, and then the cells were washed with phosphate buffer solution (PBS) twice. The cells washed with the phosphate buffer solution were fixed with 10% NBF (neutral buffered formalin), and then the nucleus was stained (Hoechst 33342, blue). After that, whether or not the cell permeable peptide-bone differentiation inducing sequence conjugate was differentiated into osteoblast was observed by using a confocal scanning microscope (IX 70, Olympus Co., Tokyo, Japan).

As a result, as shown in FIG. 4 (A: g, h, and i), when treated with the cell permeable peptide-bone differentiation inducing sequence conjugate of Example 1 and the bone differentiation inducing sequence of Comparative Example 2, the staining degree of phosphorylated calcium was similar even after 14 days of the incubation in the group treated with the bone differentiation inducing sequence (h) that fails in intracellular penetration as compared with the group treated with only PBS (g). Whereas, the group treated with the cell permeable peptide-bone differentiation inducing sequence conjugate (i) exhibited a relatively strong staining degree of phosphorylated calcium at a fluorescent wavelength, and thus confirmed the cell differentiation ability of the bone differentiation inducing sequence due to the cell permeable peptide.

4-4: Measurement on Cell Differentiation Ability of Cell Permeable Peptide-Bone Differentiation Inducing Sequence Conjugate Using Quantitative Real Time PCR and Electrophoresis In order to confirm cell differentiation ability of the cell permeable peptide-bone differentiation inducing sequence conjugate through bone tissue differentiation marker genes, human mesenchymal stem cells (hMSC) were seeded in each well of a 6 cm-dish at $1 \times 10^5$/well, and then incubated in a general medium for 20 hours (overnight) for cell stabilization. After 20 hours of incubation, the cells were treated with the cell permeable peptide-bone differentiation inducing sequence conjugate and 10 µm of the bone differentiation inducing sequence of Comparative Example 2 for 72 hours.

After that, the entire RNA was separated from the treated cells, using a Trizol® reagent (reagent for isolating RNA from cell and tissue samples) (Invitrogen Life Technologies, USA), according to the manufacturer's instructions, and the amount and purity of the entire RNA were measured by the spectrophotometer. The synthesized oligo dT 2 µl was added to 1 µg of the RNA separated from the cells, and then the distilled water was added to reach a total volume of 11 µl. The mixture was denatured at 65° C. for 10 minutes, and then quenched on the ice. SuperScriptII® Reverse Transcriptase (a MMLV RT (Moloney Murine Leukemia Cirus Reverse Transcriptase) (Invitrogen, USA) 1 µl, 100 mM DTT 2 µl, 2.5 mM dNTPs (25 mmol/l dATP, 25 mmol/l dCTP, 25 mmol/l dGTP, 10 mmol/l dTTP) 2 µl, and 5× strand buffer (reaction buffer) 4 µl were added thereto, and then maintained at 42° C. for 60 minutes. PCR was carried out by adding 1 µl of 2 pmole primers (Table 1) complementary to respective genes to the Taq-polymerase Mixture (Bioneer, Korea) while 50 ng of complementary DNC (cDNA) synthesized by the experimental method was used as a template. The repetition number for the PCR cycle was determined by using the Gene Amp PCR system 9700 (Applied Biosystems, USA) on conditions that respective PCR products were not saturated. The synthesized PCR products were subjected to electrophoresis in the 1% agaros gel containing 10 µg ml-1 of ethidium bromide (EtBr), and confirmed by using the GEL DOC™ GEL DOC 2000 (densitometer) and an image analysis system (Bio-Rad, USA).

In order to carry out the quantitative real-time PCR, cDNA to be used as a template and primers were mixed, like in RT-PCR, and then 10 µl of SYBR® Green Premix Ex Taq (TaKaRa, JAPAN) was mixed therewith to prepare a reaction material. The reaction material was annealed at 95° C. for 10 seconds, followed by 40 cycles of 95° C. for 5 seconds and 60° C. for 34 seconds, to obtain the threshold cycle (CT) value. The CT value of each gene was divided by the CT value for housekeeping GAPDH gene and the value calculated based on the negative control was taken, so that comparison in the degree of mRNA expression was conducted (Shin et al., (2007) Plant J. 49, 981-994).

As shown in FIG. 4, when treated with the cell permeable peptide-bone differentiation inducing sequence conjugate of Example 1 and the bone differentiation inducing sequence of Comparative Example 2, ALP, OCN, and RUNX2, known as bone differentiation marker genes, exhibited almost similar expression values (B) and bands (C) even after 14 days of incubation in the group treated with the bone differentiation inducing sequence that fails in intracellular penetration as compared with the group treated with only PBS. Whereas, the group treated with the cell permeable peptide-bone differentiation inducing sequence conjugate of Example 1 containing the PTD sequence of Comparative Example 1 exhibited relatively increased marker expression amounts by 2.5 fold to 60 fold and noticeably increased bands, and thus confirmed the cell differentiation ability of the bone differentiation inducing sequence due to the cell permeable peptide.

TABLE 1

Primers Used in PCR Analysis

| gene name | direction | sequence |
| --- | --- | --- |
| alkaline phosphatase (ALP) | FP | GACCCTTGACCCCCACAAT (SEQ ID No. 18) |
| | RP | GCTCGTACTGCATGTCCCCCT (SEQ ID No. 19) |
| Osteocalcin (OCN) | FP | GAAGCCCAGCGGTGCA (SEQ ID No. 20) |
| | RP | CACTACCTCGCTGCCTCC (SEQ ID No. 21) |
| Runt-related transcription factor 2 (RUNX2) | FP | CCGGCAAGATGAGCGAGGTCA (SEQ ID No. 22) |
| | RP | GTGGGTTGGAGAAGCGGCTCT (SEQ ID No. 23) |
| Glyceraldehyde-3-phosphate dehydrogenase (GAPDH) | FP | GAAGGTGAAGGTCGGAGT (SEQ ID No. 24) |
| | RP | GAAGATGGTGATGGGATTTC (SEQ ID No. 25) |

4-5: Measurement on Cell Differentiation Ability of Cell Permeable Peptide-Bone Differentiation Inducing Sequence Conjugate Using Western Blot Assay In order to confirm cell differentiation ability of the cell permeable peptide-bone differentiation inducing sequence conjugate, using proteins serving an important role in signal transduction pathways in the cytoplasmic fraction and the nuclear fraction, human mesenchymal stem cells (hMSC) were seeded in each well of a 10 cm-dish at $1 \times 10^6$/well, and then incubated in a general medium for 20 hours (overnight) for cell stabilization. After 20 hours of the incubation, the cells were treated with the cell permeable peptide-bone differentiation inducing sequence conjugate and the bone differentiation inducing sequence of Comparative Example 2 of 10 µm for each for 1.5 hours.

After that, in order to compare the expression degree of intercellular protein, in each of the cells treated with the cell permeable peptide-bone differentiation inducing sequence conjugate of Example 1 and the bone differentiation inducing sequence of Comparative Example 2, cytoplasm and nucleus were separated using NE-PER nuclear and cytoplasmic extraction reagents according to the manufacturer's instructions (Pierce, USA). The protein in the hMSC lysis solution containing the separated cytoplasm and nucleus was determined by Bradford's assay, and then subjected to electrophoresis using 10% polyacrylamide gel at 120 volts for 4 hours. After that, the protein was transferred to a nitrocellulose membrane at 310 MA for 2 hours by using a transfer buffer (12.5 mM Tris, 0.1M glycine, pH 8.3). The membrane was then blocked with a blocking solution (5% Nonfat dry milk, in TBS), and then the primary antibody solution (Smurf1, phosphoSmad1/5/8; Cell Signaling, USA, RUNX2, Lamin B, Actin; Santa Cruz, USA) was added to the blocking solution to have a concentration of 1 μg/Ml. Then, the reaction was allowed to proceed at 4° C. overnight. The next morning, a secondary antibody for each of the primary antibodies was added to the blocking solution at a ratio of 1:2000, and then the reaction was allowed to proceed at room temperature for 1 hour. The X-ray film was sensitized in a dark room by using enhanced chemo-luminal (ECL).

As shown in FIG. 4(D), when treated with the cell permeable peptide-bone differentiation inducing sequence conjugate of Example 1 and the bone differentiation inducing sequence of Comparative Example 2, phosphorylation of Smad1/5/8, which is a main transfer protein molecule transferring a signal of differentiation into osteoblast, scarcely occurs, and RUNX2, which serves as a bone differentiation induction transcript factor in collaboration with Smad 1/5/8 in the nucleus, is barely increased, even after 1.5 hours of the incubation, in the group treated with the bone differentiation inducing sequence that fails in intracellular penetration as compared with the group treated with only PBS. Whereas, the group treated with the cell permeable peptide-bone differentiation inducing sequence conjugate of Example 1 containing the PTD sequence of Comparative Example 1 exhibited Smad 1/5/8 phosphorylation and the band showing the noticeably increased RUNX2, and thus confirmed the cell differentiation ability of the bone differentiation inducing sequence due to the cell permeable peptide. It has been reported that Smurf1 protein may be present in the cytoplasm and nucleus depending on the period of action thereof, and the experiments of the present invention had the same results. Lamin B, which is protein known to be present on the nuclear membrane, was used as a marker for confirming whether or not the cytoplasm and the nucleus are well separated. Actin was used as protein for confirming whether or not the loading amount of the entire protein is uniform.

Example 5

Measurement of Cell Proliferation Ability of Cell Permeable Peptide-Bone Differentiation Inducing Sequence Conjugate In Vitro 5-1: Measurement of Cytotoxicity of Cell Permeable Peptide-Bone Differentiation Inducing Sequence Conjugate by MTT Assay Method In order to confirm whether or not cell proliferation is affected by potential toxicity when the cell permeable peptide-bone differentiation inducing sequence conjugate and control domains are cultured with hMSC, a 3-[4,5-dimethylthiazo-2-yl]-2,5-diphenyl tetrazolium bromide thiazolyl blue (MTT) assay method was used.

The MTT assay method is a method for measuring cytotoxicity by measuring absorbance of formazan produced as mitochondrial dehydrogenases in alive and metabolically active cells reduces MTT to indicate the absorbance as a percentage based on the control group. In this case, the measured absorbance reflects a concentration of the alive and metabolically active cells. 2,3,5-triphenyl tetrazolium chloride (TTC) is reduced to formazan in live cells. The formazan is insoluble purple color, and a respiration rate may be measured by a degree of color. The absorbance of formazan is maximal at 540 nm, and the absorbance measured at this wavelength reflects the concentration of the alive and metabolically active cells. Since a linear relationship between the absorbance and the concentration of the cells is not established when a concentration of cells in well to be measured is excessively high or low, a process of determining an optimal concentration of the cells was performed.

After $1\times10^3$ human Mesenchymal Stem cells (hMSC) were plated into each well of 96-well plate, the cells were treated with the cell permeable peptide-bone differentiation inducing sequence conjugate synthesized in Example 1 and domains in Comparative Example 2 at a concentration of 10 mM and cultured in medium for forming hard tissue for 24, 48, and 72 hours.

After each of the culture times, 0.1 mg (50 μl of 2 mg/Ml) of MTT was added to each well of the plate, and the cells were further cultured at 37° C. in 5% carbon dioxide for 4 hours to reduce MTT. When the culture was completed, the medium was removed from each well using a pipette so that only about 30 μl of the medium was left in each well while being careful so that crystals formed in each well is not disturbed. In order to dissolve the formazan crystal formed in each well from which the medium was removed, 150 μl of dimethyl sulforoxide (DMSO, Aldrich Com.) was added to each well and stirred for about 5 minutes so that the formazan crystal may be dissolved, and then absorbance was measured at 540 nm using an ELISA reader (Bio-Tek, USA).

Figure 5:
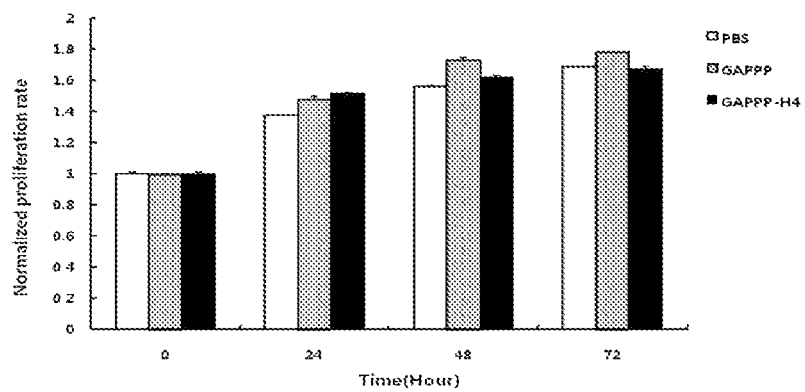
FIG. 5 is a graph showing results obtained by measuring influences of the cell permeable peptide-bioactive peptide (bone differentiation inducing sequence) conjugate according to the present invention and the comparative domains on cellular proliferation ability according to the time using an MTT reagent.

As a result, as shown in FIG. 5, when the cells were treated with the cell permeable peptide-bone differentiation inducing sequence conjugate of Example 1 and the bone differentiation inducing sequence of Comparative Example 2 while changing the culture time, the groups exhibit cell proliferation abilities similar to that of the group treated with only the PBS, and a difference of the groups was not significant. Therefore, it may be appreciated that the conjugate according to the present invention and the comparative domain did not exhibit cytotoxicity with 72 hours.

5-2: Measurement of Cytotoxicity of Cell Permeable Peptide-Bone Differentiation Inducing Sequence Conjugate by Quantitative BrdU Assay Method In order to confirm whether or not cell proliferation is affected by potential toxicity when the cell permeable peptide-bone differentiation inducing sequence conjugate and control domains are cultured with hMSC, a degree of cell proliferation was analysis by ELISA using BrdU. Since BrdU was introduced in chromosome instead of deoxy thymidine triphosphate (dTTP) at the time of DNA replication during a proliferation process of hMSC, a degree of introduction of BrdU may reflect a degree of proliferation of hMSC.

First, After $1\times10^3$ human Mesenchymal Stem cells (hMSC) were plated into each well of 96-well plate, the degree of introduction of BrdU, that is, the degree of proliferation of hMSC was measured using a cell proliferation ELISA kit (BrdU (colorimetry); Boehringermanheim, Germany). Simply describing this method, the cells were treated with the cell permeable peptide-bone differentiation inducing sequence conjugate synthesized by the method in Example 1 and the domains of Example 2 at a concentration of 10 mM and cultured in medium for forming hard tissue for 24, 48, and 72 hours. 20 l of BrdU (5-bromo-2'-deoxyuridine) was added to each of the groups before 24 hours of each culture time and further cultured for 24 hours. Formaldehyde was added thereto to fix them at room temperature for 30 minutes, and then 100 μl of anti-BrdU solution was added thereto, followed by reaction at room temperature for 90 minutes. Then, the plate was washed with PBS, and a chromogen was added thereto, followed by reaction for 30 minutes. The reaction was terminated by 1N $H_2SO_4$, and then absorbance was measured using the ELISA reader (Bio-Tek, USA) at 450 nm.

Figure 6:
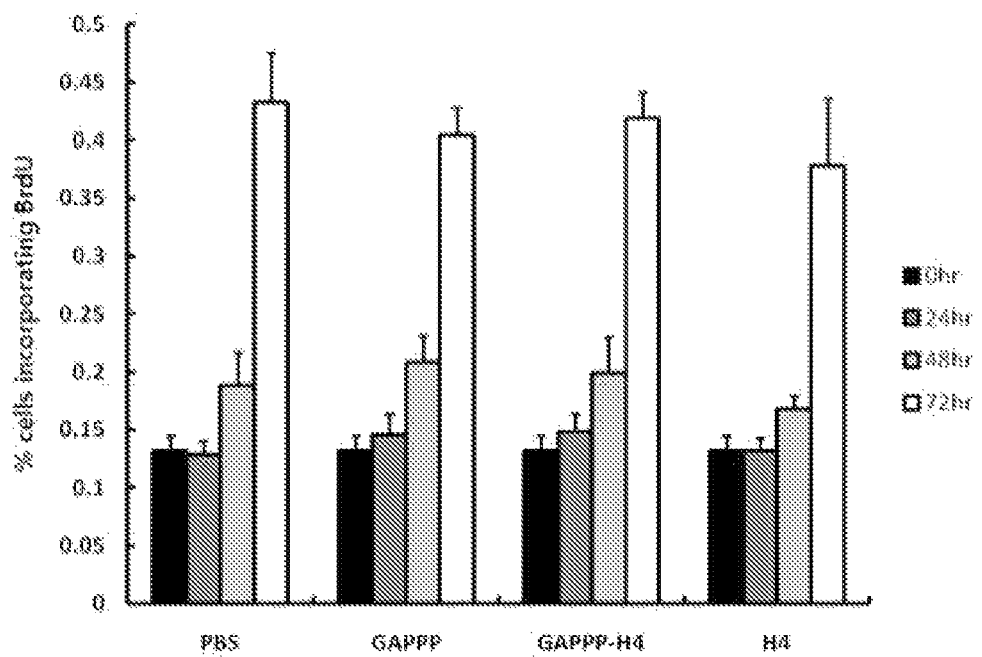
FIG. 6 is a graph showing results obtained by measuring an influence of the cell permeable peptide-bioactive peptide (bone differentiation inducing sequence) conjugate according to the present invention and the comparative domains on the cellular proliferation ability according to the time using a BrdU assay.

As a result, as shown in FIG. 6, when the cells were treated with the cell permeable peptide-bone differentiation inducing sequence conjugate of Example 1 and the bone differentiation inducing sequence of Comparative Example 2 while changing the culture time, the groups exhibit DNA synthesis abilities similar to that of the group treated with only the PBS, and a difference of the groups was not significant. Therefore, it may be appreciated that the conjugate according to the present invention and the comparative domain did not affect the cell proliferation within 72 hours.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

INDUSTRIAL APPLICABILITY

According to the present invention, cationic cell permeable peptides derived from human bone morphogenetic protein-4 have no toxicity and immuno-genicity and thus exhibit high stability as compared to viral peptide delivery vehicles, and may transport cell impermeable material into cells and into an organism without any damage to cell or material, thereby significantly increasing target gene expression. In addition, the peptide may be applied to clinical use without having to undergo a large number of processes and mass-produced, such that the present invention may be useful in the development of a drug delivery system and treatment technologies using said peptide.

The invention claimed is:

1. An isolated cell permeable peptide consisting of the amino acid sequence set forth in SEQ ID NO. 1.

\* \* \* \* \*

UNITED STATES PATENT AND TRADEMARK OFFICE
CERTIFICATE OF CORRECTION

PATENT NO.         : 9,023,987 B2
APPLICATION NO.    : 13/821790
DATED              : May 5, 2015
INVENTOR(S)        : Chong-Pyoung Chung It is certified that error appears in the above-identified patent and that said Letters Patent is hereby corrected as shown below:

In the Specification

Column 12, line 20: "TB ST" should be -- TBST --.

Column 16, lines 25 and 65: "50 mg/M1" should be -- 50 mg/Ml --.

Column 19, line 17: "1 μg/M1" should be -- 1 μg/Ml --.

Column 20, line 25: "2 μg/M1" should be -- 2 mg/Ml --.

Signed and Sealed this
Thirtieth Day of June, 2015

Michelle K. Lee
*Director of the United States Patent and Trademark Office*